(12) United States Patent
Brewer et al.

(10) Patent No.: US 6,904,314 B1
(45) Date of Patent: Jun. 7, 2005

(54) AUTOMATIC DEFIBRILLATION THRESHOLD TRACKING

(75) Inventors: James E. Brewer, Lino Lakes, MN (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 283 days.

(21) Appl. No.: 10/119,590

(22) Filed: Apr. 9, 2002

(51) Int. Cl.$^7$ ................................................ A61N 1/39
(52) U.S. Cl. ................................................ 607/7
(58) Field of Search ................................... 607/1–28

(56) References Cited

U.S. PATENT DOCUMENTS

| | | | |
|---|---|---|---|
| 5,350,410 A | 9/1994 | Kleks et al. | 607/28 |
| 5,564,422 A | 10/1996 | Chen et al. | 128/697 |
| 5,713,945 A | 2/1998 | Fischer et al. | 607/122 |
| 5,902,325 A | 5/1999 | Condie et al. | 607/28 |
| 6,169,921 B1 | 1/2001 | KenKnight et al. | 607/4 |
| 6,175,766 B1 | 1/2001 | Bornzin et al. | 607/28 |
| 6,188,927 B1 | 2/2001 | Lu et al. | 607/17 |
| 6,751,502 B2 * | 6/2004 | Daum et al. | 607/8 |
| 2003/0083712 A1 * | 5/2003 | Rueter et al. | 607/28 |

OTHER PUBLICATIONS

Splett, V. et al., "Determination of Pacing Capture in Implantable Defibrillators: Benefit of Evoked Response Detection Using RV Coil to Can Vector," Abstract Only, National Library of Medicine, Pacing Clin. Electrophysiol, Nov. 2000.

Val–Mejias, J.E., et al., "Capture Threshold Correlates with Defibrillation Threshold," Europace 2001, pp. 595–600.

* cited by examiner

Primary Examiner—Scott M. Getzow

(57) ABSTRACT

An implantable cardiac stimulating device employs an automatic defibrillation threshold tracking process that uses a measured pacing stimulation threshold to estimate the patient's defibrillation threshold on a dynamic, ongoing basis, using changes in the defibrillation threshold to re-calculate new defibrillation parameters (e.g., energy settings) on a periodic basis as a patient's heart changes over time. The defibrillation threshold estimation formula may involve a variety of variables, such as, for example, the patient's age and/or gender, and may include a selected safety margin. New defibrillation parameters are loaded into the appropriate locations of the device's memory, replacing the prior parameters, and are thereafter available for use by the device for defibrillation therapy. The defibrillation threshold tracking technique may be used in an external device, such as a programmer or external cardiac stimulation device.

51 Claims, 9 Drawing Sheets

|  | MEN | WOMEN |
|---|---|---|
| PATIENTS | 74(86%) | 12(14%) |

|  | $\mu \pm \sigma$ | RANGE |
|---|---|---|
| AGE (YEARS) | 64 ± 12 | 23-85 |
| EJECTION FRACTION | 0.34 ± 0.13 | 0.05-0.70 |

|  | RV | RV + SVC |
|---|---|---|
| LEAD CONFIGURATION | 45 (52%) | 41 (48%) |

|  | I | II | III | IV |
|---|---|---|---|---|
| NYHA CLASS | 33% | 29% | 21% | 17% |

FIG. 8

|  | $\mu \pm \sigma$ | RANGE |
|---|---|---|
| DFT ENERGY (J) | 10 ± 5.4 | 3.1-30.2 |
| DFT VOLTAGE (V) | 453 ± 118 | 265-800 |
| SHOCK IMPEDANCE (Ω) | 51 ± 11 | 34-85 |
| SHOCK PULSE WIDTH (MS) | 11 ± 2 | 5-18 |
| CYCLE LENGTH (MS) | 204 ± 32 | 145-335 |
| PACING CAPTURE VOLTAGE (V) | 0.6 ± 0.5 | 0.2-4.0 |
| PACING CAPTURE IMPEDANCE (Ω) | 572 ± 111 | 350-910 |

FIG. 9

AUTOMATIC DEFIBRILLATION THRESHOLD TRACKING

CROSS REFERENCE TO RELATED APPLICATION

This application contains subject matter that is related to copending U.S. patent application Ser. No. 10/437,110, entitled IMPLANTABLE CARDIOVERTER DEFIBRILLATOR WITH AUTOMATIC ADJUSTMENT OF SHOCK ENERGY CONTENT, filed May 13, 2003.

FIELD OF THE INVENTION

The field of the present invention generally relates to methods and apparatus for cardiac stimulation and, more particularly, to implantable defibrillators and other similar devices.

BACKGROUND

Patients with congestive heart failure ("CHF") are often treated by surgical implantation of a cardiac stimulation device (such as an implantable cardioverter-defibrillator, or "ICD") providing one or more stimulation therapies, such as pacing, cardioversion or defibrillation. Such patients generally experience a progressive, increasingly deteriorating, cardiac disease state. Over time, the substrate and function of the heart for a CHF patient changes, notably for the worse.

The changes in a patient's cardiac characteristics over time are likely to affect detrimentally the operation of an implantable cardiac stimulation device. In particular, the defibrillation threshold ("DFT") parameter determined by the physician at the time of device implant changes over time, typically in the direction of an increasing defibrillation threshold. A concern of an attending physician is whether he or she has programmed a sufficient safety margin into the implanted device to compensate for a possibly dramatic upward shift in the patient's DFT. Many patients are brought back to the hospital within a 3 to 6 month period following implant to determine whether there has been a significant shift upwards and whether the patient's DFT requires adjustment accordingly. A physician may be faced with the prospect of replacing the existing implanted device with one that provides a higher defibrillation energy to meet the higher energy requirement (comprising both the DFT value and the safety margin). The patient is continually placed at risk, and there are significant additional costs incurred as part of a regular follow-up procedure for managing the care of significantly ill CHF patients.

Some attempts have been made at predicting patients' defibrillation threshold changes overtime, but such attempts have been largely confined to the clinical setting. For example, several studies have evaluated clinical variables for the prediction of defibrillation thresholds, using transvenous leads to deliver biphasic defibrillating shocks. More than 40 clinical variables have been assessed, including demographic, electrocardiographic, echocardiographic, and radiographic measurements. However, these clinical parameters are not intrinsic to the cardiac stimulation field.

It would therefore be advantageous to provide an implantable cardiac stimulation device capable of automatically determining a patient's defibrillation energy threshold and related defibrillation parameters, taking account of the changing nature of a patient's cardiac characteristics over time.

SUMMARY OF THE INVENTION

The invention in one aspect is generally directed to an apparatus and method for dynamically adjusting defibrillation parameters in an implantable device, based upon certain related parameters measured automatically by the device while operating after implantation.

In one aspect, an automatic defibrillation threshold tracking process includes the steps of determining a pacing stimulation threshold, and estimating the patients defibrillation threshold dynamically based upon the measured pacing stimulation threshold. The defibrillation threshold estimate, in certain embodiments, is only re-calculated if the pacing stimulation threshold differs significantly (that is, more than a programmed or preset amount) from its last measured level. The defibrillation threshold estimation formula may involve a variety of variables, such as, for example, the patient's age and/or gender, which are typically available as programmed variables. The estimated defibrillation threshold may be adjusted by a safety margin to derive the energy for the first shock attempt if defibrillation is needed. The new defibrillation parameters, if any, are loaded into the appropriate locations of the device's memory, replacing the prior parameters. The new parameters are thereafter available for use by the device for defibrillation therapy.

A cardiac stimulation device with automatic defibrillation threshold tracking is preferably programmed with predetermined time intervals that determine the operation of the defibrillation threshold tracking procedure. The predetermined time intervals may be programmed by the physician according to, for example, a defibrillation parameter adjustment schedule. The defibrillation tracking feature may be programmed to operate continuously, or it may be programmed to operate intermittently, either periodically (such as daily, weekly, or monthly), or on demand.

Further embodiments, variations and enhancements are also disclosed herein.

BRIEF DESCRIPTION OF THE DRAWINGS

FIG. 8 is a table showing demographic data of patients in an experimental study.

FIG. 9 is a table showing ventricular defibrillation and capture parameters for the patients referred to in the experimental study of FIG. 8.

DETAILED DESCRIPTION OF THE PREFERRED EMBODIMENTS

In one aspect, an automated defibrillation threshold tracker (ADTT) is disclosed that seeks to continually optimize the programmed energy settings of an implanted cardiac stimulating device, with the goal of operating the device with the minimum defibrillation energy required for reliable, safe, and effective treatment for patients in hemodynamically compromising ventricular tachycardia (VT) and/or ventricular fibrillation (VF). The automated defibrillation threshold tracker preferably operates in a feedback loop to adjust, over time, the defibrillation threshold (DFT) value originally determined or programmed at time of the device's implant. The tracking routine uses the adjusted defibrillation threshold value to adapt the minimum required defibrillation energy settings. The defibrillation threshold value and defibrillation energy settings are dynamically tracked and recalibrated continuously or periodically, depending on programmed settings.

Figure 1:
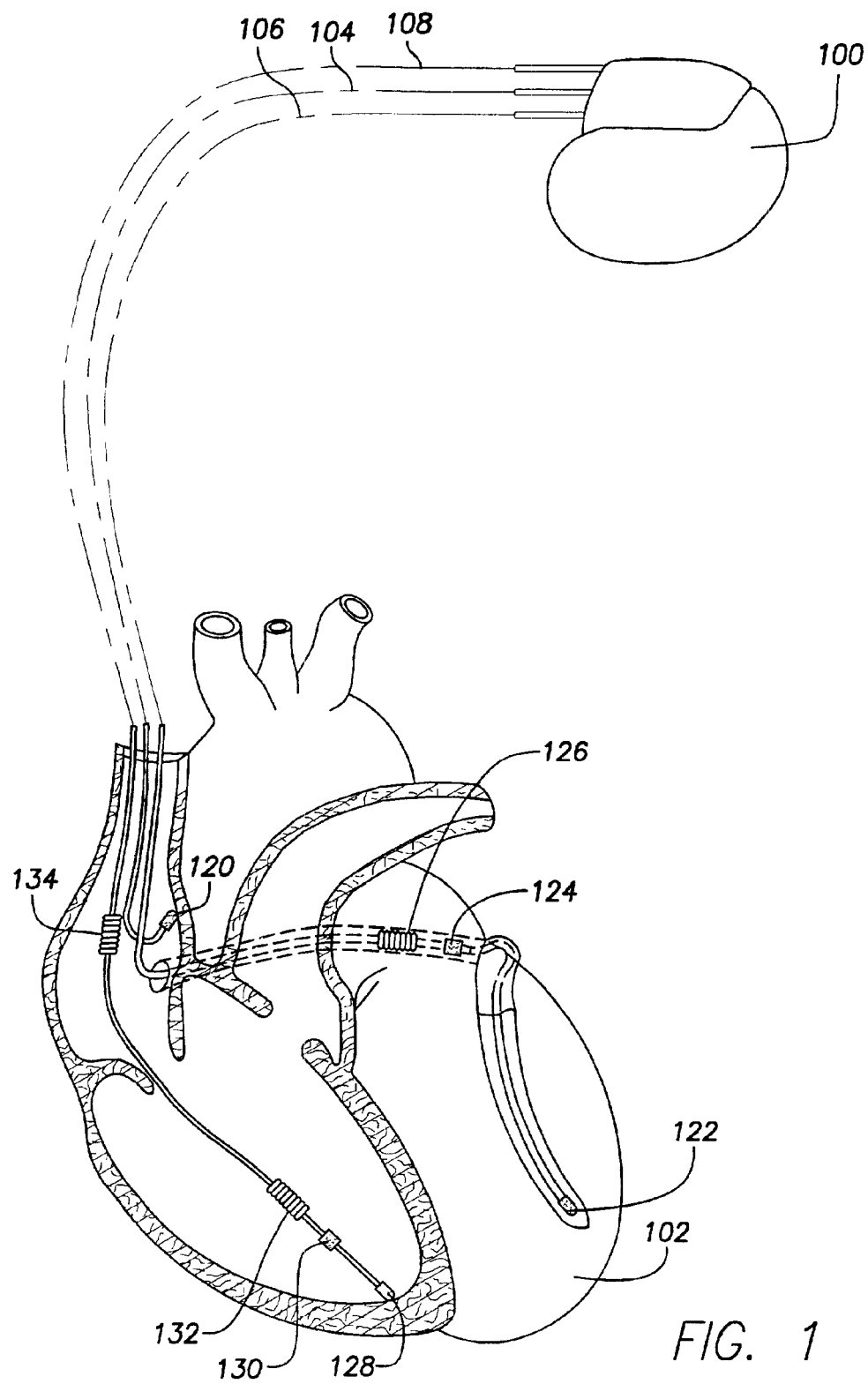
FIG. 1 is a diagram illustrating a cardiac stimulation device in communication with a patient's heart.

FIG. 1 is a simplified diagram illustrating an implantable cardiac stimulation device 100 (as may be utilized in connection with one or more embodiments disclosed herein) in communication with a patient's heart 102. In the particular example illustrated in FIG. 1, the implantable cardiac stimulation device 100 is electrically connected to the patient's heart 102 by way of three leads 104, 106, and 108, suitable for multi-chamber sensing- and delivery of stimulating pulses and/or shock therapy. Generally, the implantable cardiac stimulation device 100 senses cardiac activity in, and delivers stimulating pulses or electrical shocks to, the atria and ventricles of the patient's heart 102 via leads 104, 106, and 108.

To sense atrial cardiac signals and to provide right atrial chamber stimulation therapy, stimulation device 100 is preferably coupled to an implantable right atrial lead 104 having at least an atrial tip electrode 120, which typically is implanted in the patients right atrial appendage. To sense left atrial and ventricular cardiac signals and to provide left chamber pacing therapy, stimulation device 100 is preferably coupled to a coronary sinus lead 106 designed for placement in the coronary sinus region via the coronary sinus by positioning a distal electrode adjacent to the left ventricle and/or additional electrode(s) adjacent to the left atrium. The coronary sinus region in the present context generally refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. A preferred coronary sinus lead 106 is configured to receive atrial and ventricular cardiac signals, and to deliver left ventricular pacing therapy using a left ventricular tip electrode 122, left atrial pacing therapy using a left atrial ring electrode 124, and shocking therapy using a left atrial coil electrode 126. In each case, the electrical return path may be a different lead or the housing of the cardiac stimulation device 100 itself, according to the particular design employed.

The implantable cardiac stimulation device 100 is preferably also in electrical communication with the patient's heart 102 by way of an implantable right ventricular lead 108 having, in the exemplary implementation illustrated in FIG. 1, a right ventricular tip electrode 128, a right ventricular ring electrode/ sensor 130, a right ventricular (RV) coil electrode 132, and a superior vena cava (SVC) coil electrode 134. In typical implantations, the right ventricular lead 108 is transvenously inserted into the heart 102 in a manner such that the right ventricular tip electrode 128 is positioned in the right ventricular apex, the RV coil electrode 132 is positioned in the right ventricle, and the SVC coil electrode 134 is positioned in the superior vena cava. The right ventricular lead 108 is thereby capable of receiving cardiac signals, and delivering stimulation in the form of pacing and/or shock therapy, to the right ventricle.

Figure 2:
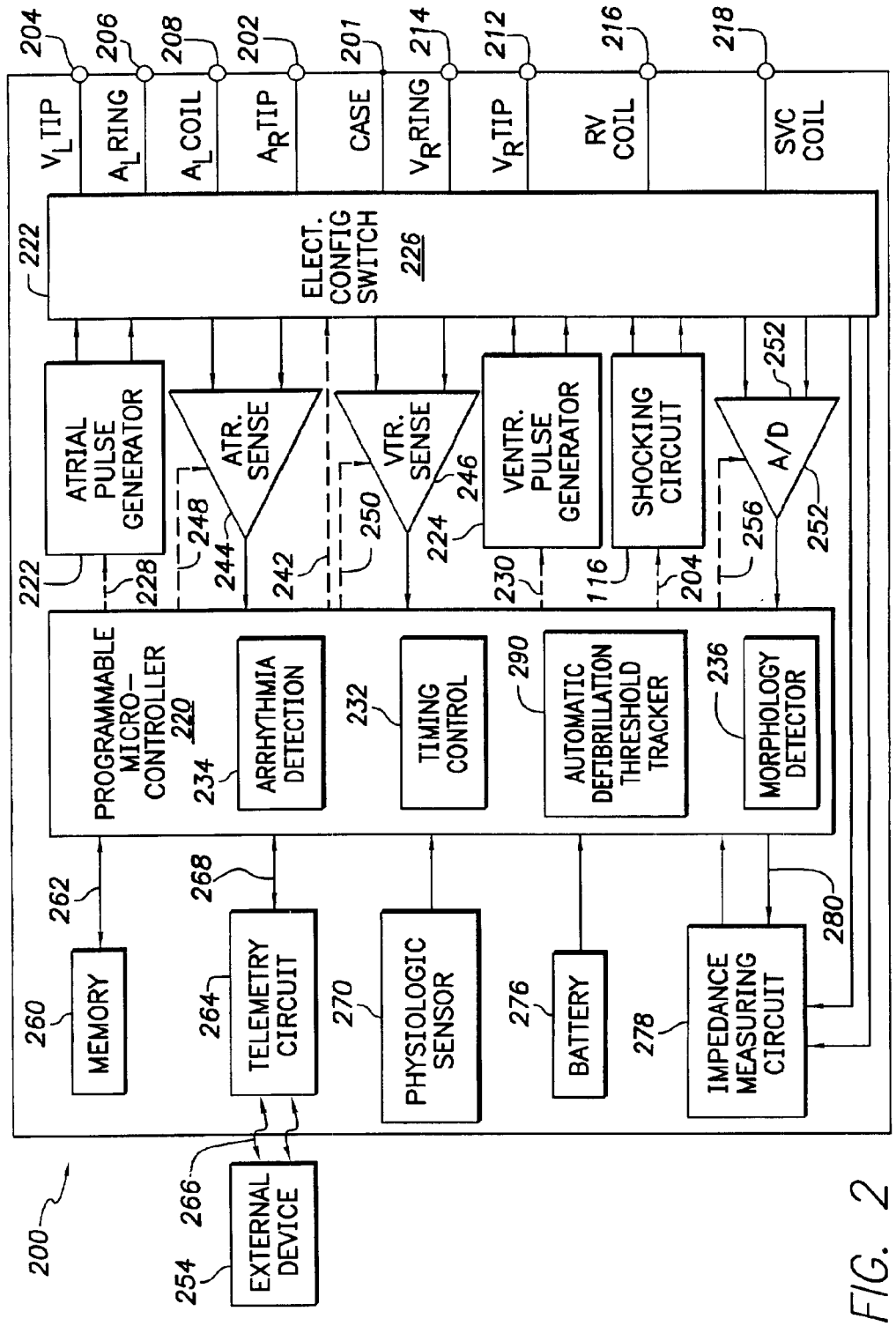
FIG. 2 is a simplified, functional block diagram depicting various components of an exemplary cardiac stimulation device according to one embodiments as disclosed herein.

FIG. 2 is a simplified, functional block diagram depicting various components of an exemplary cardiac stimulation device system 200, as may be incorporated (in whole or part) into an implantable cardiac stimulation device such as, for example, cardiac stimulation device 100 illustrated in FIG. 1. Preferably, the cardiac stimulation device system 200 is capable of providing cardioversion, defibrillation, and pacing stimulation therapies in as many as all four chambers of the patient's heart for treating fast or slow arrhythmias, or other heart conditions, although in some cases a more streamlined set of functional features will be desired. Likewise, the principles as have been and will be described herein are not only applicable to multi-chamber devices, but also to single-chamber devices. It will be understood and appreciated by those skilled in the art that various components or features in the FIG. 2 system 200 could be duplicated, eliminated, or disabled, in various combinations, while still operating according to the principles as described herein.

As described in greater detail elsewhere herein, the cardiac stimulation device system 200 preferably provides the ability to determine a pacing energy stimulation threshold, and to derive an estimated defibrillation energy threshold value for the patient based upon the determined pacing energy stimulation threshold. Such an operation is preferably carried out periodically to allow the device to adapt the shock energy levels to the patient's changing heart condition.

As illustrated in FIG. 2, among the electrical connections provided in the cardiac stimulation device system 200 is a case "electrode" connection 201 to the housing of the cardiac stimulation device. The housing for an implantable cardiac stimulation device is often referred to as the "can," "case" or "case electrode," and the case electrode connection 201 may in some cases be selected, via appropriate programming parameters, to act as the return electrode for various "unipolar" modes. The housing, through the case electrode connection 201, may further be used as a return electrode for shocking purposes, either alone or in combination with one or more coil electrodes (such as coil electrodes 126, 132 and 134 illustrated in FIG. 1). Further illustrated, from a schematic standpoint, are signal terminals 202, 204, 206, 208, 212, 214, 216 and 218 (the names of the electrodes or other component to which the terminals are intended to be attached are shown next to each terminal). Preferably, the housing of the cardiac stimulation device includes a connector (not shown) providing a means for connecting the terminals 202, 204, 206, 208, 212, 214, 216, and 218 to their respective electrodes or other components.

For right atrial sensing and pacing, the connector preferably includes a right atrial tip terminal ($A_R$ TIP) 202 adapted for connection to the atrial tip electrode 120. For left chamber sensing, pacing, and shocking, the connector preferably includes a left ventricular tip terminal ($V_L$ TIP) 204, a left atrial ring terminal ($A_L$ RING) 206, and a left atrial shocking terminal ($A_L$ COIL) 208, which are adapted for connection to the left ventricular ring electrode 122, the left atrial tip electrode 124, and the left atrial coil electrode 126, respectively.

For right chamber sensing, pacing, and shocking, the connector further preferably includes a right ventricular tip terminal (V_R TIP) 212, a right ventricular ring terminal (V_R RING) 214, a right ventricular shocking terminal (R_V COIL) 216, and an SVC shocking terminal (SVC COIL) 218, which are adapted for connection to the right ventricular tip electrode 128, right ventricular ring electrode 130, the RV coil electrode 132, and the SVC coil electrode 134, respectively.

A programmable microcontroller 220 is preferably provided in the cardiac device stimulation system 200 to, among other things, control the various modes of stimulation therapy. As is well known in the art, microcontroller 220 typically includes a microprocessor, or equivalent control circuitry, designed specifically for controlling the delivery of stimulation therapy, and may further include volatile (e.g., RAM) and/or non-volatile (e.g., ROM) memory, logic and timing circuitry, state machine circuitry, and I/O circuitry. Typically, microcontroller 220 includes the ability to process or monitor input signals (data) as controlled by a program code stored in a designated block of memory. The specific type of microcontroller 220 is not critical to the described implementations. Rather, any suitable microcontroller 220 may be used that is capable of carrying out the functions described herein. The use of microprocessor-based control circuits for performing timing and data analysis functions are well known in the art.

FIG. 2 further shows, in connection with the cardiac device stimulation system 200, an atrial pulse generator 222 and a ventricular pulse generator 224 for generating pacing stimulation pulses to be delivered by the right atrial lead 104, the coronary sinus lead 106, and/or the right ventricular lead 108, preferably via an electrode configuration switch 226. To provide stimulation therapy in each of the four chambers of the heart, the atrial and ventricular pulse generators 222, 224 may include dedicated, independent pulse generators, multiplexed pulse generators, or shared pulse generators. In the example shown in FIG. 2, the pulse generators 222, 224 are controlled by the microcontroller 220 through control signals 228 and 230, respectively, which serve the purpose of triggering or inhibiting the stimulation pulses.

The microcontroller 220 may include, in the form of, e.g., digital circuitry, microcode or program instructions, or a combination thereof, various functional blocks which facilitate control of the various aspects of the cardiac stimulation device system 200. For example, the microcontroller 220 may include timing control circuitry 232 to control the timing of the stimulation pulses (e.g., pacing rate, atrioventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc. These types of timing functions are well known in the art.

Microcontroller 220 further may include one or more of an arrhythmia detector 234, a morphology detector 236, and an automatic defibrillation threshold tracker 240. These components can be utilized by the cardiac stimulation device system 200 to detect and treat various cardiac conditions requiring treatment. The arrhythmia detector 234, morphology detector 236, and automatic defibrillation threshold tracker 240 may be implemented, e.g., in hardware as part of the microcontroller 220, or as software/firmware instructions programmed into the device and executed on the microcontroller 220 during certain modes of operation.

In the example illustrated in FIG. 2, the electronic configuration switch 226 preferably comprises a plurality of internal switches (not shown) for connecting the desired terminals (e.g., terminals 202, 204, 206, etc.) to the appropriate input/output circuits, thereby providing complete electrode programmability. The electronic configuration switch 226, in response to a control signal 242 from the microcontroller 220, determines the polarity of the stimulation pulses (e.g., unipolar, bipolar, combipolar, etc.) by selectively opening/closing the appropriate combination of internal switches, in a manner well known in the art.

To sense activity in any or all chambers of the heart, atrial sensing circuit 244 and ventricular sensing circuit 246 may be selectively coupled to the right atrial lead 104, coronary sinus lead 106, and the right ventricular lead 108, preferably through the electronic configuration switch 226. The atrial sensing circuit 244 and ventricular sensing circuit 246 may include, e.g., dedicated sense amplifiers, multiplexed amplifiers, or shared amplifiers. The electronic configuration switch 226 preferably determines the "sensing polarity" of the cardiac signal by selectively opening/closing the appropriate internal switches, in a manner well understood in the art. The foregoing features allow the clinician to program the sensing polarity independent of the stimulation polarity.

Each sensing circuit 244 and 246 preferably employs one or more low power, precision amplifiers with programmable gain and/or automatic gain control, bandpass filtering, and threshold detection circuitry, as known in the art, to selectively sense the cardiac signal of interest. The automatic gain control assists the cardiac stimulation device system 200 with sensing the typically low amplitude signal characteristics associated with atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224, respectively, in a programmable fashion in response to the absence or presence of cardiac activity in the appropriate chambers of the heart. The sensing circuits 244 and 246, in turn, receive control signals over signal lines 248 and 250 from the microcontroller 220 for purposes of controlling the gain or threshold of the sensing circuits 244, 246, any polarization charge removal circuitry (not shown), and/or the timing of any blocking circuitry (not shown) coupled to the inputs of the sensing circuits 244, 246, all in a manner well understood in the art.

For arrhythmia detection, the cardiac stimulation device system 200 may utilize the atrial and ventricular sensing circuits 244, 246 to sense cardiac signals, which can be analyzed to determine whether a particular cardiac rhythm is physiologic or pathologic. Generally, as used herein, the term "sensing" refers to the noting of an electrical signal, while the term "detection" refers to the processing of sensed signals and noting the presence of an arrhythmia or other specific cardiac event or activity. The timing intervals between sensed events (e.g., P-waves, R-waves, and T-waves) are preferably classified by the arrhythmia detector 234 of the microcontroller 220 by, e.g., comparing the intervals to predefined rate zone limits (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (preferably including bradycardia pacing, anti-tachycardia pacing, or cardioversion/defibrillation shocks, all three of which are collectively referred to as "tiered therapy").

Cardiac signals may, in addition to being applied to atrial and ventricular sensing circuits 244, 246, also be applied to inputs of an analog-to-digital (AID) data acquisition system 252. The A/D data acquisition system 252 is preferably configured to acquire intracardiac electrogram signals, convert the raw analog data into a digital signal, and store the digital data for later processing and/or telemetric transmission to an external device 254. The data acquisition system 252 may be selectively coupled to the right atrial lead 104, the coronary sinus lead 106, and the right ventricular lead 108 through the electronic configuration switch 226 to allow sampling of cardiac signals across any desired pair of electrodes.

Advantageously, the data acquisition system 252 may be coupled to the microcontroller 220, or other detection circuitry, for detecting an evoked response from the heart in response to an applied stimulus, thereby aiding in the detection of "capture." Capture occurs when an electrical stimulus applied to the heart is of sufficient energy to depolarize the cardiac tissue, thereby causing the heart muscle to contract. The microcontroller 220 generally detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed at regular intervals—e.g., once a day during at least the acute phase (e.g., the first 30 days after implantation) and less frequently thereafter. A capture threshold search procedure begins at a desired starting point (e.g., a high energy level, or else the level at which capture is currently occurring) and decreases the energy level until capture is lost. The value at which capture is lost is known as the capture threshold. Thereafter, a safety margin may be added to the capture threshold to arrive at a pacing stimulus energy value.

The microcontroller 220 is generally coupled, via a data/address bus 262, to a memory 260, wherein the programmable operating parameters used by the microcontroller 220 are stored and modified, as required, in order to customize the operation of the stimulation device 100 to suit the needs of a particular patient. Such operating parameters may define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. The memory 260 is preferably large enough to store a relatively large amount of data (e.g., from the data acquisition system 252), which may be read out at a later time (by telemetry) and used for subsequent analysis to guide the programming of the device.

Advantageously, the operating parameters of the implantable device 100 may be non-invasively programmed into the memory 260 through a telemetry circuit 264 in telemetric communication via communication link 266 with an external device 254, such as a programmer, transtelephonic transceiver, or a diagnostic system analyzer. The microcontroller 220 activates the telemetry circuit 264 with a control signal 268. The telemetry circuit 264 may allow intracardiac electrograms (ECGs) and status information relating to the operation of the device 100 (as contained in the microcontroller 220 or memory 260) to be sent to the external device 254 through an established communication link 266.

The cardiac stimulation device system 200 can further include one or more physiologic sensors 270, such as a "rate-responsive" sensor which is used to adjust pacing stimulation rate according to the state of exertion of the patient. The physiological sensor 270 may alternatively, or in addition, be used to detect changes in cardiac output, changes in the physiological condition of the heart, or diurnal changes in activity (e.g., detecting sleep and wake states). The microcontroller 220 may be programmed to respond to information received from the physiologic sensor 270 by, e.g., adjusting the various pacing parameters (such as rate, AV Delay, V—V Delay, etc.) at which the atrial and ventricular pulse generators 222, 224, generate stimulation pulses, or by making other dynamic adjustments. While shown in FIG. 2 as being included within the stimulation device, the physiologic sensor 270 may instead be external to the stimulation device, yet still be implanted within or carried by the patient. Examples of physiologic sensors that may be implemented in cardiac stimulation device system 200 include sensors that, for example, sense respiration rate and/or minute ventilation, pH of blood, ventricular gradient, and so forth. The physiological sensor 270 may also be embodied, for example, with reference to FIG. 1, as a pressure sensor that is coupled to detect RV pressure that is sensed by a sensor located at ring 130, which can perform dual functions of a ring electrode and a pressure sensor.

The one or more physiological sensors 270 may further include sensors for detecting position or postural changes. Any sensor capable of sensing such changes, either directly or indirectly, may be used for such a purpose. In particular, the one or more physiological sensors 270 may include an activity or position sensor (not shown) mounted within the housing of the stimulation device to detect movement in the patient's position. The activity or position sensor may be implemented in many ways, including as a 3D accelerometer, a sensor that detects the earth's magnetic or gravitational fields, a MEMs (micro-electro mechanical) device, and the like. Another sensor that may be used is of the type that detects activity variance.

The cardiac stimulation device system 200 additionally includes a battery 276 for providing operating power to the circuitry shown in FIG. 2. For an implantable cardiac device employing cardioversion or defibrillation shock therapy, the battery 276 is preferably capable of operating at low current drains (preferably less than, e.g., 10 $\mu$A) for long periods of time, and of providing high-current pulses (for capacitor charging) when the patient requires a shock pulse. The battery 276 also desirably has a predictable discharge characteristic so that elective replacement time can be detected. As one example, the battery 276 may be of the lithium/silver vanadium oxide variety.

The cardiac stimulation device system 200 can further include magnet detection circuitry (not shown), coupled to the microcontroller 220, to detect when a magnet is placed in near proximity to the cardiac stimulation device. A magnet may be used, for example, by a clinician to perform various test functions of the cardiac stimulation device and/or to signal the microcontroller 220 that the external programmer 254 is in place to exchange data with the microcontroller 220 through the telemetry circuits 264.

The cardiac stimulation device system 200 further may include an impedance measuring circuit 278, enabled by the microcontroller 220 via a control signal 280. Examples of uses for an impedance measuring circuit 278 include, among other things, (1) lead impedance surveillance during the acute and chronic phases for proper lead positioning or dislodgment; (2) electrode operability verification (and automatic switching to an operable pair if dislodgment occurs); (3) measurement of respiration or minute ventilation; (4) measurement of thoracic impedance for determining shock thresholds; (5) detection of whether the device has been implanted; (6) measurement of stroke volume; and (7) detection of the opening of heart valves. The impedance measuring circuit 278 is advantageously coupled to the electronic configuration switch 226 so that any desired electrode may be used in connection with the impedance measuring circuit 278.

In the case where the cardiac stimulation device system 200 is intended to be a part of an implantable cardioverter/defibrillator (ICD) device, the cardiac stimulation device system 200, upon detecting the occurrence of an arrhythmia, automatically applies a programmed electrical shock therapy to the heart aimed at terminating the detected arrhythmia. To this end, the microcontroller 220 controls a shocking circuit 282 through a control signal 284 (or set of control signals). The shocking circuit 282 may be programmed to generate shock pulses of different selectable energy magnitudes—for example, of low (up to 0.5 joules), moderate (0.5–10 joules), or high energy (11 to 40 joules)—as controlled by the microcontroller 220. Such shock pulses are ordinarily applied to the patient's heart through at least two shocking electrodes, which, referring now to FIG. 1, may be selected from the left atrial coil electrode 126, the RV coil electrode 132, and/or the SVC coil electrode 134. The housing of the cardiac stimulation device may act as an active electrode in combination with the RV electrode 132, or as part of a split electrical vector using the SVC coil electrode 134 or the left atrial coil electrode 126 (i.e., using the RV electrode as a common electrode).

Figure 3:
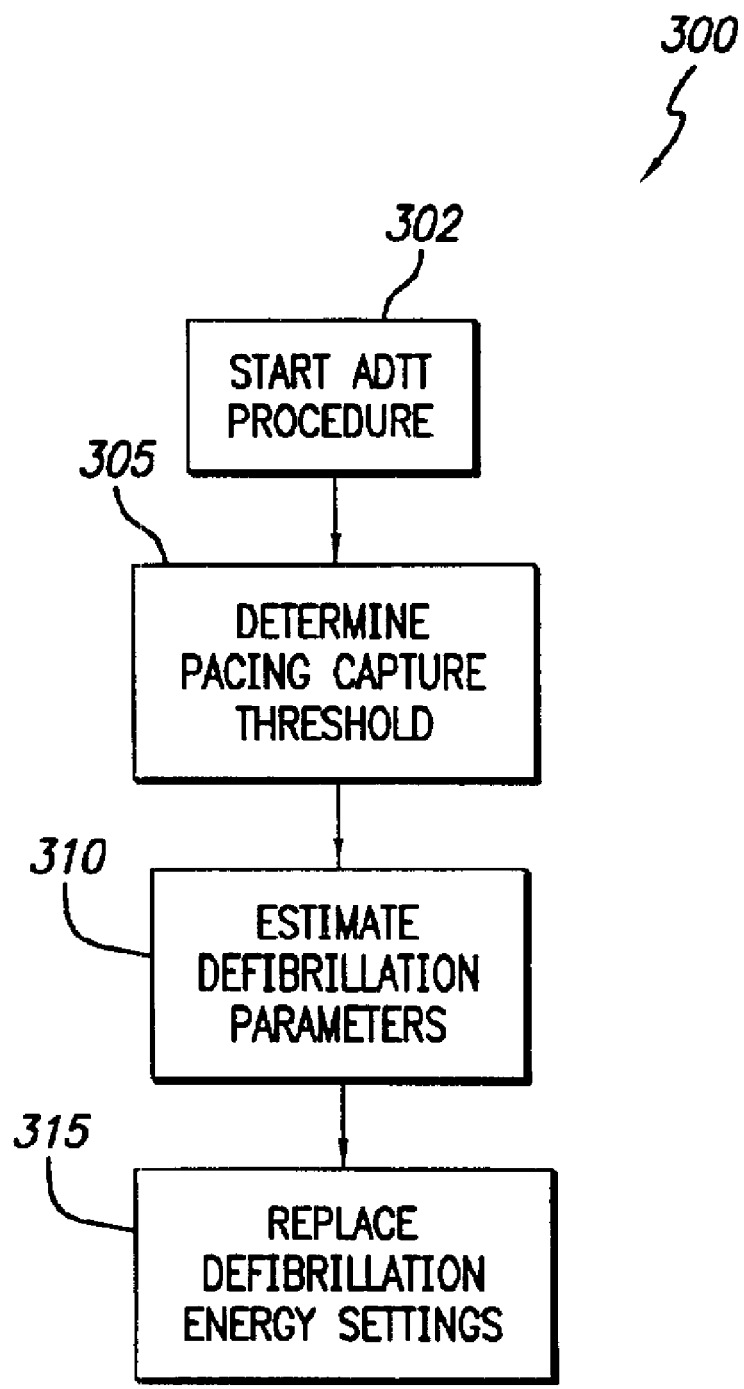
FIG. 3 is a high level process flow chart for automatic defibrillation threshold tracking.

Cardioversion shocks tend to be of low to moderate energy level (so as to minimize pain felt by the patient), and may be synchronized with an R-wave. Cardioversion therapy tends to be utilized, generally, for the treatment of tachycardia. Defibrillation shocks are generally of moderate to high energy level (e.g., in the range of 5–40 joules), delivered synchronously or asynchronously (since R-waves may be too disorganized during a fibrillation episode). Defibrillation shocks are generally utilized for treating fibrillation. The microcontroller 220 is preferably capable of controlling the synchronous or asynchronous delivery of the shock pulses, and the provision of synchronous or asynchronous shocks may be either programmable (and may further be tailored to the particular mode or degree of therapy) or may be set by default in whole or part According to a preferred embodiment, a cardiac stimulation device is configured to automatically track the chronic (i.e., long-term) changes in a patient's defibrillation threshold over time. The measured changes in the patient's capture threshold are preferably used to estimate the changes in the defibrillation threshold. A generalized flow diagram of a preferred method for automatic defibrillation threshold tracking is illustrated in FIG. 3. As shown therein, in a first step 302, the automatic defibrillation threshold tracking process is started. The process may be initiated according to a programmed schedule—e.g., periodically. At the start of an operational cycle, the automatic defibrillation threshold tracking feature may initiate a subsystem that determines the value of the capture threshold, using the pacing lead and electrode portion of the implanted lead configuration to detect an evoked response of the heart to an applied pacing stimulus. Thus, as indicated in step 305, the capture threshold for pacing is determined, using any of a variety of conventional techniques, examples of which are explained in greater detail hereinafter.

In step 310, new defibrillation parameters (e.g., the defibrillation energy threshold and possibly the defibrillation shock characteristics) are estimated, or re-calculated, based upon the measured capture threshold. In some instances, the defibrillation parameters are only estimated or re-calculated if the measured capture threshold differs significantly (that is, more than a programmed or preset threshold amount) from the last measured capture threshold. The automatic tracking feature may estimate the energy defibrillation threshold value using the capture threshold value output from the step 305 and a preselected estimation formula. The selected defibrillation threshold estimation formula may involve additional variables, such as, for example, a patient's age (adjusted for length of implant time) and gender, which are available as programmed variables. The first shock energy may also be adjusted using a pre-selected safety margin method (for example, adding 10 joules to the threshold estimate, or multiplying it by 2).

Lastly, in step 315, the new defibrillation parameters, if any, are loaded into the appropriate locations of the device's memory, replacing the prior parameters. The new parameter(s) are thereafter available use by the device for defibrillation therapy.

Automatic defibrillation threshold tracking is preferably included as a feature within an ICD platform. At the time a patient receives an implantable cardiac stimulation device (e.g., ICD), the physician preferably activates the automatic defibrillation threshold tracking ("ADTT") feature. The physician may do so, for example, by way of commands sent over a telemetry link. Once the automated defibrillation threshold tracking feature has been activated, the implanted device cycles through the tracking procedure each time it is initiated by the device's microcontroller.

The cardiac stimulation device is preferably programmed with predetermined time intervals that determine the initiation of the defibrillation threshold tracking procedure. The predetermined time intervals may be programmed by the physician according to, for example, a defibrillation energy adjustment schedule. The defibrillation tracking feature may be programmed to operate continuously, or it may be programmed to operate intermittently, either periodically (such as daily, weekly, or monthly), or on demand.

One technique for configuring the defibrillation threshold tracking feature to operate "on demand" is to separate the first measuring/determining step of the defibrillation tracking process (that is, step 305 in FIG. 3) operationally from the later steps of the process. Step 305 is then initiated on a different, more frequent schedule than the remaining steps in the process. Steps 310 and 315 are only performed if the capture threshold estimated in step 305 is different from a previously-stored value by a predetermined significant amount If the capture threshold is significantly different from the stored capture threshold value, then steps 310 and 315 of the automatic defibrillation threshold tracking procedure are performed, and the new capture threshold replaces the previously stored capture threshold value.

Figure 7:
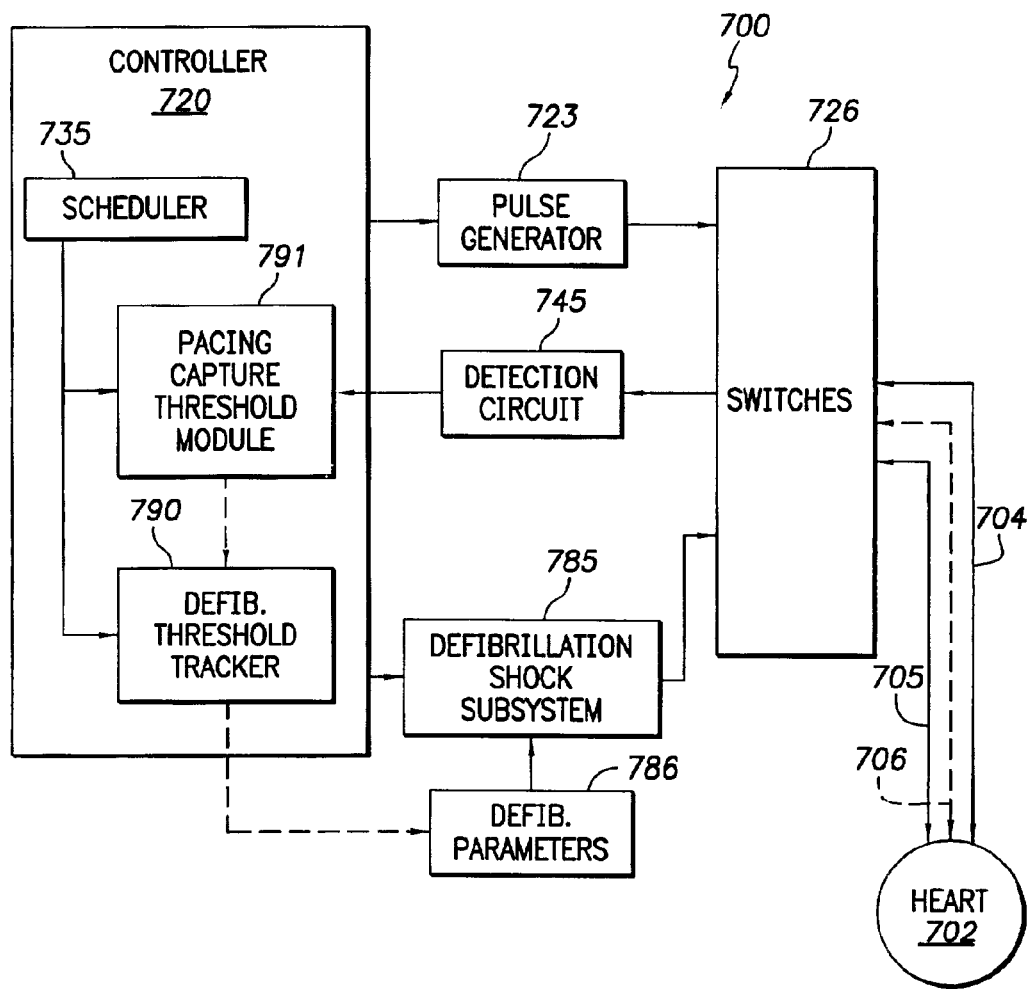
FIG. 7 is a high level block diagram illustrating certain functional components of an implantable cardiac stimulation device in accordance with a preferred embodiment as disclosed herein.

FIG. 7 is a high-level block diagram illustrating certain functional components of an implantable cardiac stimulation device 700 in accordance with a preferred embodiment as disclosed herein. As shown in FIG. 7, the implantable cardiac stimulation device 700 comprises a pulse generator 723 for delivering stimulating pulses to a patients heart 702 through various leads 704, 705, and 706 (the number of leads being dependent in part on the nature of the implantable cardiac stimulation device 700). A detection circuit 745 detects the evoked response from the patient's heart 702 in response to applied stimulating pulses. The pulse generator 723 and detection circuit 745 may be connected to the patient's heart 702 through a set of switches 726 which selectively connect the leads 704, 705, and/or 706 to the pulse generator 723 and detection circuit 745. Also selectively connectable to the leads 704, 705, and/or 706 is a defibrillation shock subsystem 785, which may comprise, e.g., high voltage charging circuitry, high voltage energy storage means (such as one or more capacitors, typically in the range of 90–120 $\mu$F), a sub-controller for managing the charge-up and discharge of the high voltage energy storage means, and/or any other suitable circuitry for generating defibrillating (or cardioverting) shocks to the patient's heart 702.

The implantable cardiac stimulating device 700 further comprises a controller 720 which manages and controls the basic functions of the device 700. The controller 720 may comprise, for example, a microprocessor, memory, input/output ports, timing circuitry, and any other circuitry. As relevant to the embodiment depicted, the controller 720 may comprise a pacing threshold capture module 791, a defibrillation threshold tracker 790, and a scheduler 735. In this embodiment, the scheduler 735 is programmed to control the initiation of the pacing capture threshold process and the defibrillation threshold determination. For example, the scheduler 735 may utilize one or more programmable scheduling interval parameters, and may invoke the pacing capture threshold module 791 and the defibrillation threshold tracker 790 periodically, at timing intervals dictated by the one or more programmable scheduling interval parameters. With multiple parameters, the pacing capture threshold module 791 may be invoked with a different frequency (generally more often) than the defibrillation threshold tracker 790.

When invoked by the scheduler 735, the pacing capture threshold module 791 conducts a routine for determining the patient's pacing energy stimulation threshold (or "capture threshold"). Examples of such routines are described elsewhere herein. After the pacing energy stimulation threshold has been determined by the pacing capture threshold module 791, the defibrillation threshold tracker 790 may be automatically invoked, or else may be invoked after a certain number of times the pacing capture threshold module 791 has been invoked, or else may be invoked upon demand— e.g., only if the pacing energy stimulation threshold deviates materially from its prior value. A material deviation may be indicated by the determined pacing energy stimulation threshold differing more than a programmable amount (which can be a fixed amount or percentage) from its prior value. Once invoked, the defibrillation threshold tracker 790 calculates or estimates one or more defibrillation-related parameters, such as the patient's defibrillation energy threshold value, according to any of the various techniques as described elsewhere herein.

The specific components of the pulse generator 723, detection circuit 745, defibrillaton shock subsystem 785, controller 720, and switches 726 may be implemented, in one embodiment, in a manner as shown in and previously described in greater detail with reference to FIG. 2, or in any other suitable manner.

Advantages of defibrillation threshold tracking as described herein are several fold, including more reliable and effective defibrillation therapy and extended battery life (by tailoring the shock energy to that which is specifically needed by the patient).

The actual determination of the defibrillation energy threshold based upon the determined pacing energy stimulation threshold may depend upon a number of different factors, such as, for example, the characteristics of the pacing pulses used to determine the pacing energy stimulation threshold, the type and/or placement of electrodes, and other variables. The defibrillation energy threshold value may, in a particular embodiment, be determined according to an equation of the general form:

$$DFT=K1+(K2 \times CPT)$$

where "DFT" represents the estimated defibrillation energy threshold value, "CPT" represents the pacing energy stimulation threshold, and "K1" and "K2" are selected coefficients. The coefficients K1 and K2 may be determined by experimentation for the particular type of pacing pulses used, the type and/or placement of the electrodes, and so on. The coefficients may also be tailored for the particular type of defibrillating waveform. For example, the coefficients K1 and K2 may take on a set of first values for a monophasic defibrillating waveform, and a set of second values for a biphasic defibrillating waveform (or a set of third values for a triphasic defibrillating waveform). The coefficients may also be adjusted further if there are other variables involved in the defibrillating shock characteristics. For example, a 6/3 ms biphasic waveform might have slightly different coefficients than a 4/2 ms biphasic waveform. Also, using larger electrodes, such as the RV coil and the "can" (i.e., device outer housing), for the pacing threshold test may also more accurately simulate the defibrillation shock.

The estimates derived using the estimating equations are preferably bounded within preset or programmable limits. For example, the automatic defibrillation threshold tracking routine, or a subsequent defibrillation shock parameter setting procedure, may use lower and upper limiting thresholds to bound the defibrillation threshold estimates, or alternatively the subsequently generated defibrillation shock energy settings, above a minimum value and below a maximum value. The limiting thresholds are preferably determined based upon the pacing and defibrillating characteristics of an implantable device, and may have different values for different leads, lead placements, and/or different implantable device characteristics.

In a preferred embodiment, the coefficients K1 and K2 are adjustable, through remote programming, at the time of implantation, based upon the patient's actual measured defibrillation energy threshold. The physician may either program the coefficients K1 and K2 directly, or else enter the patient's actual measured defibrillation threshold which then is used for automatic re-calculation or tuning of the coefficients K1 and K2.

Figure 10:
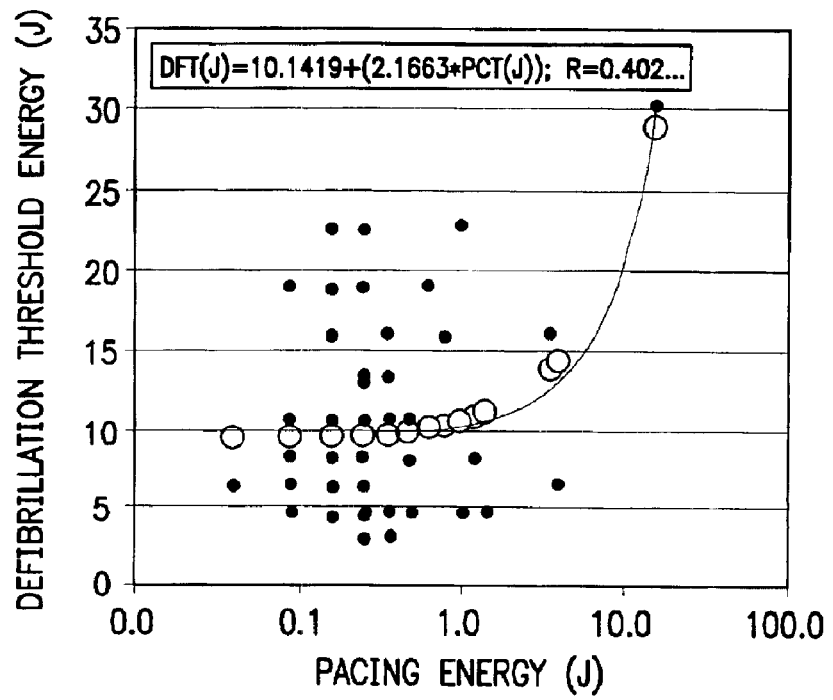
FIG. 10 is a graph illustrating the relationship of pacing energy needed for capture with the patient's defibrillation energy threshold in the experimental study.
Figure 11:
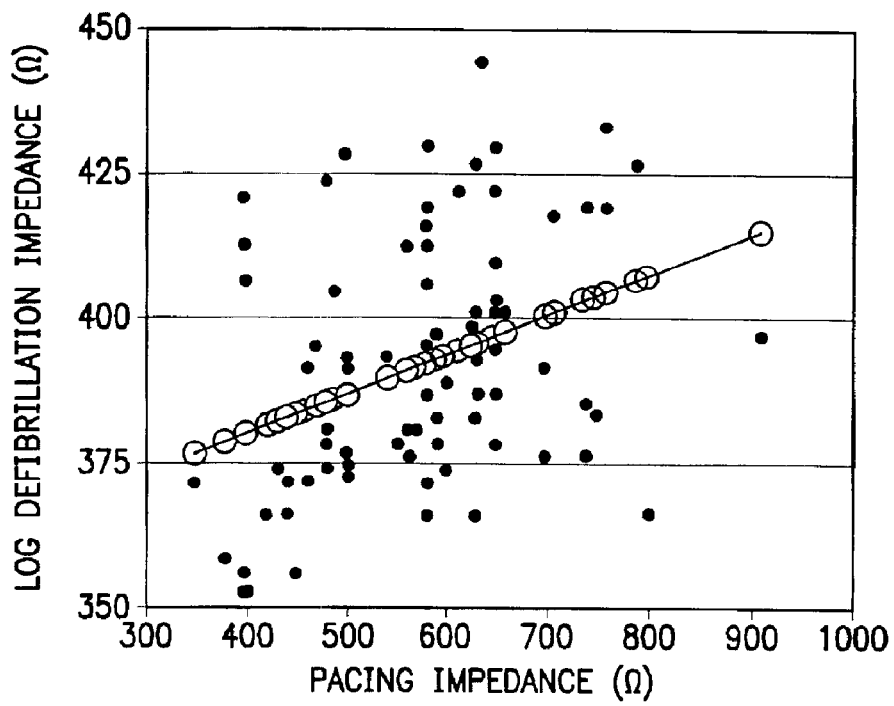
FIG. 11 is a graph illustrating the relationship between pacing impedance and defibrillation impedance based upon the experimental data.

Experimental data were used to derive a regression model for one particular implementation. Details regarding the experimental data and manner in which they were obtained is described in a paper entitled "Capture Threshold Correlates with Defibrillation Threshold" (Monduzzi Editore S.p.A. 2001) by J. E. Val-Mejias, J. E. Brewer, and M. W. Kroll, the latter two of whom are inventors of the instant application. FIG. 8 lists demographic data of the patients, and FIG. 9 lists the ventricular defibrillation and capture parameters for the particular patient group. FIG. 10 is a graph illustrating the relationship of pacing energy (in joules) needed for capture with the patient's defibrillation energy threshold (in joules), and FIG. 11 is a graph illustrating the relationship between pacing impedance and defibrillation impedance based upon the experimental data. From the experimental data, a relationship between a patient's energy DFT (in joules) and the energy capture threshold (CPT) can be derived, as expressed according to the estimating equation:

$$DFT(J)=10.1+(2,200 \times CPT(J))$$

with a correlation factor of R=0.40. The above is the same form of equation as previously set forth herein, with coefficients K1=10.1 (or about 10) and K2=2,200 (or about 2,000), the latter of which is relatively large because the energy capture threshold (CPT) is typically on the order of microjoules. More generally, given the fact that conditions may vary, coefficient K1 would be expected to be acceptable in the range of about 9 to 11, and coefficient K2 would be expected to be acceptable in the range of about 1,000 to 3,000, based upon the experimental data previously mentioned. The experimental data involved the use of a biphasic defibrillation waveform, but a similar technique can be used to develop an estimating equation for other types of waveforms (e.g., monophasic or triphasic).

Alternatively, the defibrillation energy threshold can be related to the pacing energy stimulation threshold according to a similar equation, reflected in volts (rather than joules), in which case the equation may take the form of:

$$DFT(V)=K1+(K2 \times CPT(V)^2)$$

where "DFT(V)" represents the estimated defibrillation energy threshold value (in volts), "CPT(V)" represents the pacing energy stimulation threshold (in volts), and "K1" and "K2" both represent selected coefficients. Thus, in the above example, given the experimental data, the estimating equation relating pacing stimulation threshold and defibrillation energy threshold may be set out as:

$$DFT(V)=453+(38 \times CPT(V)^2)$$

More generally, given the fact that conditions may vary, coefficient K1 in the above equation would be expected to be acceptable in the range of about 400 to 500, and coefficient K2 would be expected to be acceptable in the range of about 25 to 50, based upon the experimental data previously mentioned. Since some physicians may prefer programming in terms of shock energy (joules) while other physicians may prefer programming in terms of shock voltages, in certain embodiments it may be desirable to allow the physician to select which units are to be used for the automatic defibrillation threshold tracking and shock energy/strength adjustment.

Alternatively, the defibrillation energy threshold, in terms of energy (e.g., joules), may be derived from the capture threshold voltage directly, taking advantage of the relationship between voltage and energy and the effect of regression analysis on certain terms in the relevant equations. Thus, the defibrillation energy threshold value may, for example, be determined according to an equation of the general form:

$$DFT(J)=K1+(K2 \times CPT(V)^2)$$

where "DFT(J)" represents the estimated defibrillation energy threshold value (in joules), "CPT(V)" represents the pacing energy stimulation threshold (in volts), and "K1" and "K2" both represent selected coefficients. In the present example, based upon the experimental-data, the estimating equation relating pacing stimulation threshold voltage and defibrillation energy threshold may be approximated as:

$$DFT(J)=10.1+(2,200 \times CPT(V)^2)$$

As before, given the fact that conditions may vary, coefficient K1 would, more generally, be expected to be acceptable in the range of about 9 to 11, and coefficient K2 would be expected to be acceptable in the range of about 1,000 to 3,000, based upon the experimental data previously mentioned.

A potentially more accurate relationship between pacing energy stimulation threshold and defibrillation energy threshold can be drawn taking account of additional variables, such as the patient's age/or and gender. In such a case, the defibrillation energy threshold can be related to the pacing energy stimulation threshold according to an equation of the general form:

$$DFT=K1+(K2 \times CPT)-(K3 \times V1)-(K4 \times V2) \ldots (KN \times V(N-2))$$

where "DFT" again represents the estimated defibrillation energy threshold value (in joules), "CPT" again represents the determined pacing energy stimulation threshold (in joules), K1, K2 . . . KN represent selectable coefficients, and V1, V2, . . . V(N–2) represent variable parameters (such as the patient's age, gender, etc.). A similar equation with expanded terms to take account of additional variables (such as age and gender) can be expressed with the equation terms reflected in volts instead of joules, using the square of the pacing capture threshold energy, and making appropriate adjustments to the coefficients.

Using, for example, the experimental data previously mentioned, and the gender and age of the patient as variables, the defibrillation energy threshold can be approximately related to the capture threshold by the equation $$DFT(J)=10.1+((2,100 \times CPT(J))-(1.1 \times Age)-(1.1 \times Gender))$$

or alternatively, $$DFT(J)=10.1+((2,100 \times CPT(V)^2)-(1.1 \times Age)-(1.1 \times Gender))$$

where Gender in this example equals 1 for a male and 2 for a female patient, and CPT is in terms of joules (first equation) or volts (second equation), with a correlation factor of R=0.49. As before, given the fact that conditions may vary, coefficient K1 would, more generally, be expected to be acceptable in the range of about 9 to 11, coefficient K2 would be expected to be acceptable in the range of about 1,000 to 3,000, based upon the experimental data previously mentioned. Also, coefficients K3 and K4 would be expected to be acceptable in the range of about 0.5 to 1.5.

With different leads and/or placement and different implantable device characteristics, different coefficients may be derived for the above estimating equations. Since each device/lead configuration generally undergoes at least some amount of clinical trials, a ready source of experimental data is available for collection and analysis to arrive at a suitable estimating equation for the particular device/lead combination. With different leads and/or lead placements and/or different implantable device characteristics, different minimum and maximum limiting values for the estimated defibrillation threshold values and/or energy settings may also be derived for the estimating equations.

The correlation between the pacing energy stimulation threshold and the estimated defibrillation threshold energy value can potentially be increased in accuracy by using pacing pulses of similar shape to the desired defibrillating shock pulses and of different duration than ordinary pacing pulses, and by delivering the pulses via the defibrillating electrodes. Pacing pulses are nominally monophasic in nature and typically approximately 0.5 milliseconds in length. However, because of the common practice of recharging the output capacitor through the tissue to maintain a zero average current (to forestall corrosion), there is typically a low current second phase of reversed polarity. This second phase portion is typically in the area of 5 ms in the atrial channel and 12 ms in the ventricular channel. To derive an estimated defibrillation threshold energy value for a biphasic defibrillating shock, it may be desirable to apply pacing pulses which are more similar to the biphasic defibrillation shocks (which commonly have a wider first phase and a more narrow second phase). Further, for defibrillating shocks of any shape, it may be desirable to change the duration of the pacing pulses to, e.g., 5 milliseconds. To enhance accuracy by allowing the pacing pulses to be applied to the same myocardial tissue as the defibrillating shocks will, if necessary, later be applied, the switches 726 (see FIG. 7) may be configured to allow low voltage pacing pulses to be delivered through the defibrillation electrodes, for the purposes of running a pacing energy stimulation threshold capture routine with results that may bear a stronger correlation to defibrillation.

Preferably, the implantable cardiac stimulating device 700 is one in which the leads 704, 705, and/or 706 are integrated (in which the pacing anode is the defibrillating cathode). As a result, pacing stimulation energy threshold measurements are more likely to vary in direct proportion to the patient's defibrillation energy threshold.

Figure 4:
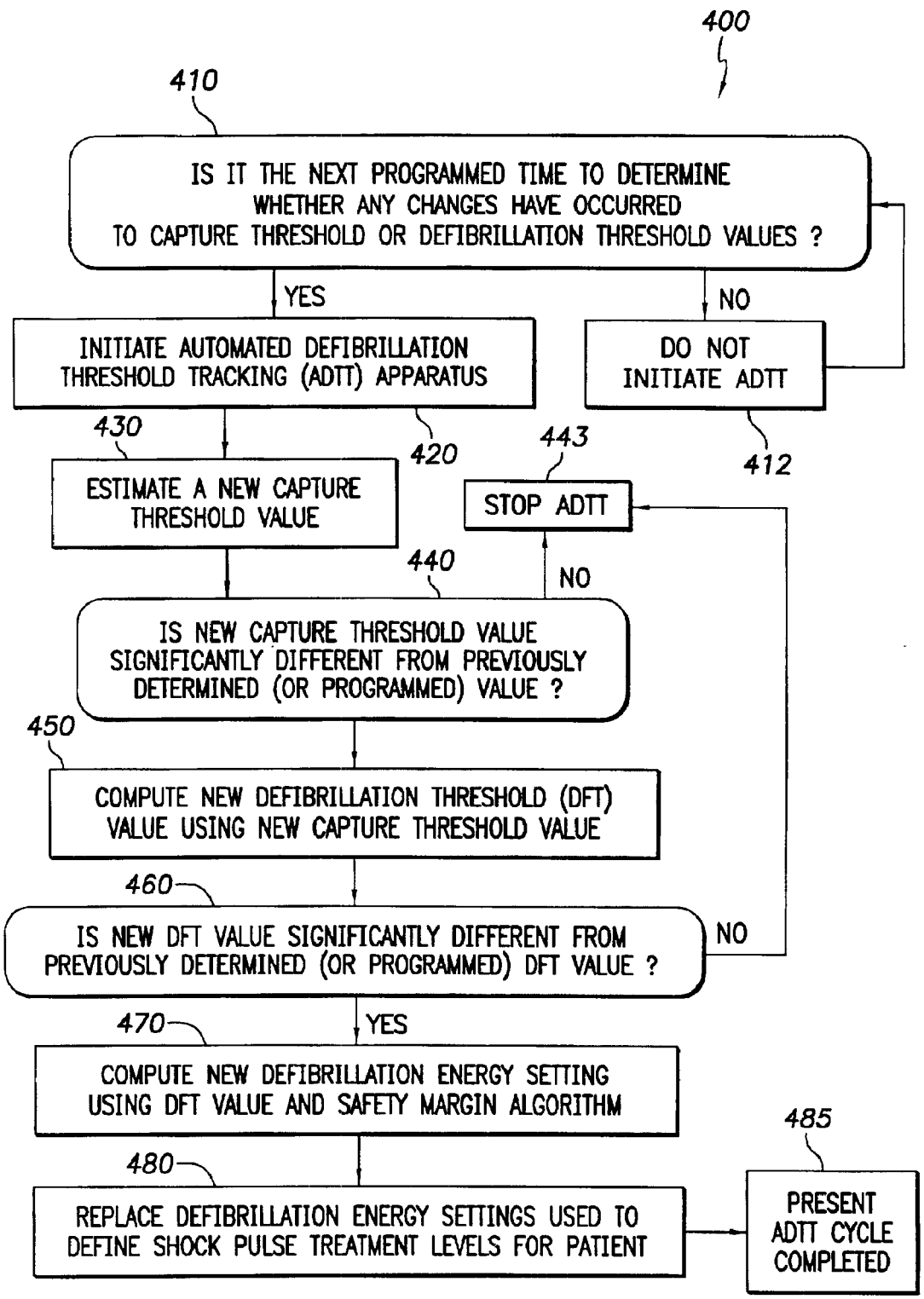
FIG. 4 is a more detailed process flow chart for automatic defibrillation threshold tracking.

FIG. 4 illustrates a more detailed process flow, in accordance with one embodiment, for tracking a patient's defibrillation threshold and deriving a new capture threshold and, if necessary or desired, a new defibrillation threshold and energy settings. In this example, the operation of the automatic defibrillation threshold tracking process is periodic and driven by a preprogrammed schedule, permitting an ongoing adjustment to the defibrillation energy settings. The periodic operation is, e.g., preprogrammed at the factory according to best clinical practices and may be adjusted or amended by a physician at time of implant or any time thereafter with the use of a programmer. With reference to the embodiment illustrated in FIG. 4, the automatic defibrillation threshold tracking routine of the implantable cardiac stimulating device remains inactive (steps 410 and 412, repeating) until a time-out of the programmed time interval has occurred, according to the preprogrammed schedule. During this time, the implantable cardiac stimulating device may carry out its ordinary and conventional functions. When the time-out of the programmed interval has occurred, the automatic defibrillation threshold tracking routine is initiated, at which point it initializes all necessary software variables and hardware components, as indicated by step 420. The automatic defibrillation threshold tracking routine next proceeds to estimate a new capture threshold, as indicated by step 430, using an appropriate pacing energy stimulation threshold determination process. In step 440, assuming the process is configured to operate in an "on demand" fashion, the automatic defibrillation threshold tracking routine determines whether the capture threshold is significantly different (in either percentage or absolute terms) from its previously stored value. A predetermined threshold differential may serve as a means for determining whether a difference is significant As an example, the capture threshold may be deemed to be significantly different, for the purposes of the automatic defibrillation threshold tracking routine, when the new value differs from the old value by more than five percent.

If the difference in capture threshold is significant, the automatic defibrillation threshold tracking routine next, as indicated by step 450, computes a new defibrillation energy threshold value using the energy capture threshold value according to a programmed equation (or look-up table or other suitable means). For example, the routine may calculate the defibrillation energy threshold using a regression-determined estimator, such as $DFT(J)=10.1+(2,200 \times CPT(J))$, or a multivariate regression estimator, such as the formula $DFT(J)=10.1+((2,100 \times CPT(V)^2)-(1.1 \times Age)-(1.1 \times Gender))$, where $CPT(V)$ is defined as the pacing capture threshold (in volts), age is measure in years, and the gender variable is defined to be 1 for a male patient and 2 for a female patient. Attentively, one of the other types of estimating equations disclosed herein may be used. Other techniques for determining the defibrillation energy threshold estimates from the capture voltage may be developed, for example, from clustering techniques, Bayesian classifier techniques, fuzzy modeling, neural networks, or nonlinear regression formulations, such as logistic regression or projection pursuit regression. In each case, the appropriate relationship may be constructed by the application of relevant clinical data to appropriate model-building software, and from the relationship an embedded routine within the automatic defibrillation threshold tracking subsystem may be formulated to derive the defibrillation threshold estimates.

Optionally, as indicated by step 460 in FIG. 4, the automatic defibrillation threshold tracking routine then checks to determine whether the new defibrillation energy threshold value is significantly different from a previously stored or programmed defibrillation energy threshold value, again preferably using a (different) threshold differential, either percentage or absolute in terms. If the difference in old and new defibrillation energy threshold values is significant, the automatic defibrillation threshold tracking routine computes the new defibrillation energy settings, as indicated by step 470, and, as indicated by step 480, replaces the present operational values with the newly estimated values. The automatic defibrillation threshold tracker then shuts itself off until the next time the implantable cardiac stimulating device initiates the activity.

Figure 5:
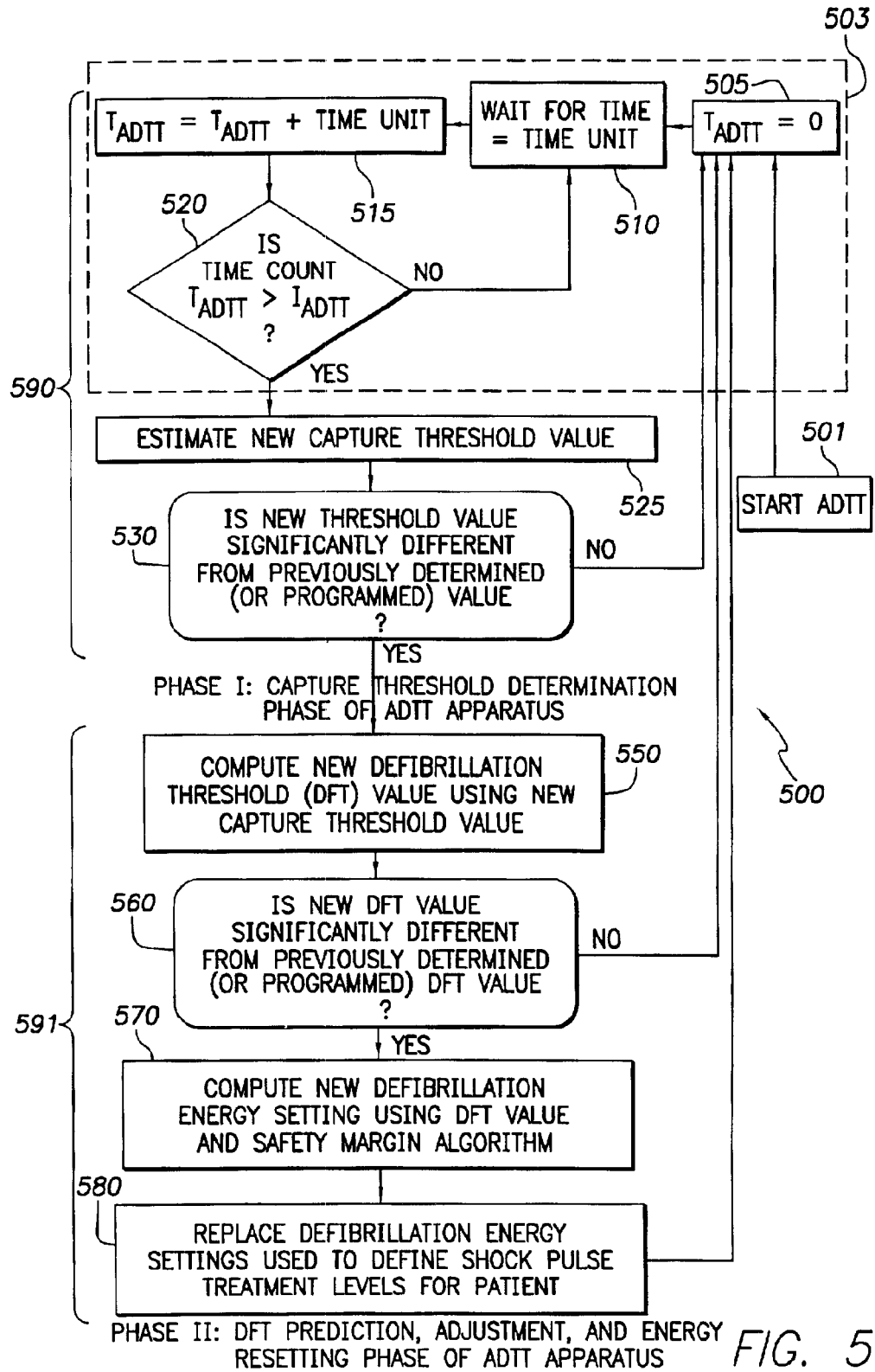
FIG. 5 is another process flow chart, in accordance with an alternative embodiment, for automatic defibrillation threshold tracking.

FIG. 5 is a process flow diagram illustrating an example of an automatic defibrillation threshold decision algorithm that controls the implantable cardiac stimulating device in an "on demand" type of operational mode, first determining whether the capture threshold has changed significantly, and then, if so, adjusting the defibrillation energy settings in tandem with the patient's changing defibrillation energy threshold. As illustrated in FIG. 5, the process 500 can be conceptually divided into two main stages, a first stage 590 in which the pacing capture threshold is determined, and a second stage 591 in which the defibrillation energy threshold and new energy settings are determined. At the start of the first stage 590, as indicated by step 501, the automatic defibrillation threshold tracking feature is initialized by setting an initial defibrillation energy threshold value as determined by the physician, e.g., during the implant procedure. The process 500 then enters a timing loop 503 which governs the periodic determination of the pacing capture threshold and the decision as to whether a new defibrillation energy threshold value should be generated. Those skilled in the art will appreciate that many different types of timing loops can be implemented or substituted without departing from the principles and concepts described herein. For example, a dedicated timer may be used for the timing loop 503, or a system timer may be used, with a periodic comparison being made with the time contained in the system timer. The timer may count forwards or backwards, and may count upwards from zero or from a current time value, or backwards to zero from the desired count value. The timer itself, if counting backwards, may generate a flag or other signal when reaching zero. Alternatively, whether the timer is counting forwards or backwards, a comparator, loaded with the target timing value, may be used to generate a time-out signal when the desired target timing value has been reached. The timing loop 503 may be independent for the pacing capture threshold and/or defibrillation energy threshold tracking process, or may be combined with other activities that the cardiac stimulation device carries out as part of its periodic "housekeeping" duties (such as, for example, checking the status of various system components).

In the particular timing loop example illustrated in FIG. 5, the timing of the automatic defibrillation threshold tracking feature can be programmed in terms of a particular time unit (e.g., seconds, minutes, etc.), which will typically be much longer than the clocking rate of the device's system clock. The available time unit(s) may be physician-selectable, and the frequency of monitoring the patient's defibrillation energy threshold will therefore be based upon the physician's preference. The timing loop 503 utilizes a dedicated timing variable $T_{ADTT}$ which is set to zero and then incremented until a target timeout period, indicated by the programmable variable $I_{ADTT}$, is reached. According, in step 505, the timing variable $T_{ADTT}$ is set to zero, and then, in step 510, a timer then counts for one time unit. At the end of each time unit, the timing variable $T_{ADTT}$ is incremented by the amount equal to the time unit. In step 520, the timing variable $T_{ADTT}$ is compared against the programmed variable $I_{ADTT}$, which, as noted, indicates the target time-out period. In the present example, if $T_{ADTT}$ exceeds the target time-out variable $I_{ADTT}$, then the process 500 moves forward to steps 525 and 530, whereupon the cardiac stimulation device determines a new pacing capture threshold and determines whether the new pacing capture threshold differs significantly from its previous value. If not, the timing loop 503 is restarted.

If the pacing capture threshold is determined to significantly differ from its previous value (by a predetermined differential, whether fixed, percentage, or otherwise), the process then moves to the second stage 591, wherein the defibrillation energy threshold and new energy settings, if necessary, are determined. The steps 550, 560, 570, and 580 in process 500 are largely analogous to steps 450, 460, 470, and 480, respectively, described earlier with respect to FIG. 4.

The steps illustrated in the processes 400 and 500 illustrated in FIG. 4. and FIG. 5, respectively, may be carried out by a controller internal to the cardiac stimulation device—for example, microcontroller 220 shown in FIG. 2, or controller 720 shown in FIG. 7. Alternatively, the steps may be carried out by a subsystem or dedicated hardware or firmware (including a finite state machine).

Examples of pacing threshold capture, as may be utilized in various embodiments, will now be described. In one or more embodiments, the pacing threshold capture techniques as described in U.S. Pat. No. 6,175,766 to Bornzin et al, may be utilized. As described in that patent, an implantable cardiac stimulation device automatically initiates, at predetermined times, or under command by the external programmer, an automatic pacing energy stimulation threshold search routine for a particular chamber of the heart (e.g., right atrium, right ventricle, etc.). In carrying out the automatic threshold search, the pulse generator of the implantable cardiac stimulation device repeatedly applies pairs of stimulating pacing pulses to the selected heart chamber. Each pair of stimulating pulses includes a first pulse which is of lesser energy (i.e., lesser in magnitude and/or duration) than the second pulse. Nevertheless, the first-applied pulse is chosen to be of sufficient energy so as to readily assure capture of the selected heart chamber at the start of the routine.

The first and second pulses of each pulse pair evoke a first response and a second response, respectively, of the selected heart chamber. After each pulse pair is applied to the heart chamber, the first response and the second response are compared to provide capture values. More specifically, the second response is subtracted from the first response to provide capture values. When the first pulse of a pulse pair is of sufficient energy to capture the heart chamber, the capture value will be substantial, relatively constant, and of a particular polarity. However, when the amplitude of a first pulse in a pulse pair drops below the capture threshold, the capture value subtraction will yield a capture value which is of the opposite polarity. When this occurs, the capture threshold of the selected heart chamber will be deemed to be the amplitude of the first pulse in the last pulse pair that succeeded in capturing a response from the heart chamber.

It may be noted that, even though the first pulse in the last applied pulse pair will not capture the heart, the second pulse of that pulse pair is greater in energy than the first pulse, and so the second pulse will still generally be of sufficient energy to evoke a cardiac response so as to maintain cardiac rhythm management of the patient.

Figure 6:
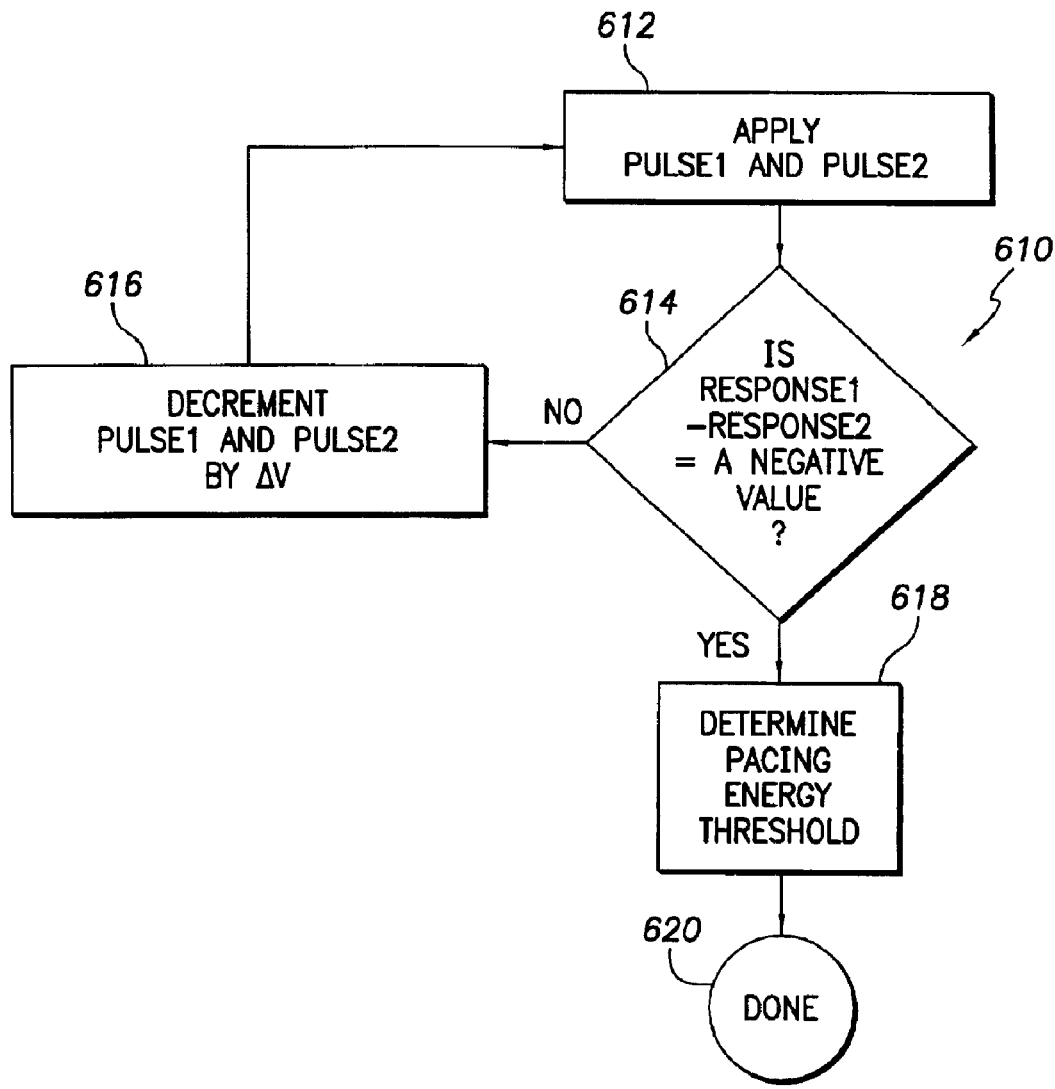
FIG. 6 is a block diagram of a cardiac device system including a capability for determining a pacing energy stimulation threshold.

FIG. 6 illustrates a flow diagram 610 which essentially summarizes the methodology described above. When the implantable cardiac stimulation device enters the automatic pacing threshold search routine, it applies the pulse pair as indicated by 612, with the energy of the first pulse being less than the energy of the second pulse. The first pulse and the second pulse will evoke first and second responses respectively of the heart chamber. As indicated by 614, the second response is subtracted from the first response to yield a capture value. If the capture value is not negative, that will mean the first pulse captured the chamber and the second pulse evoked the polarization response. As a result, the energies of the first and second pulses are decremented in accordance with step 616 and the process 610 returns to step 612.

When the capture value in step 614 is negative, the process 610 then moves to step 618 wherein the pacing energy stimulation threshold of the selected chamber is determined. As previously indicated, the pacing energy threshold may be determined as being the energy of the first pulse of the last pulse pair capturing the selected chamber (plus the incremental energy resolution of the pulse generator). Once the capture threshold is determined in accordance with step 618, the pacing threshold capture process is completed.

Additional details regarding pacing threshold capture are described in U.S. Pat. No. 6,175,766, which is hereby incorporated by reference in its entirety.

Another example of pacing threshold capture is described in U.S. Pat. No. 5,350,410 to Kleks et al, hereby incorporated by reference as if set forth fully herein. That patent describes an autocapture system within an implantable cardiac stimulation device to automatically maintain the energy of a stimulation pulse at a level just above that needed to capture myocardial tissue by pacing. A loss-of-capture ("LOC") routine is employed during a capture verification test to increase the energy of pacing pulses by a predetermined amount following a failure to match an electrical post-stimulation signal from the heart to a polarization template. Periodically, or at programmed intervals, the capture verification test is performed to calibrate a set of energy-related polarization template parameters. A capture verification test such as described in the Kleks et al patent may be used in connection with various embodiments as disclosed herein.

Other techniques may also be used for pacing threshold capture. For example, if desired, various techniques as described in U.S. Pat. No. 5,902,325 (hereby incorporated by reference as if set forth fully herein) may be used for pacing threshold capture.

In various embodiments as described herein, any type of suitable pacing electrodes and/or leads may be used. One type of useful lead is described U.S. Pat. No. 5,713,945 to Fischer et al. As described therein, an implantable lead may be constructed with a radioisotope material incorporated in it, in order to decrease the rate of fibrotic growth. The rate of fibrotic growth is known to be an important variable with respect to the chronic stability of a patient's capture threshold and defibrillation energy threshold values. Therefore, a preferred implantable cardiac stimulation device with automatic defibrillation threshold tracking incorporates a radioisotope-releasing pacing and defibrillation lead, so as to provide a more stable biological interface for tracking defibrillation threshold changes over time. The increased stability of the biological interface, and the resulting increased stability of the pacing and defibrillation thresholds, permit the automatic defibrillation threshold tracking operation to be performed less frequently and with enhanced accuracy.

The techniques described herein can be used for either atrial or ventricular defibrillation threshold tracking (and defibrillation energy level adjustment), or both. The atrial defibrillation energy threshold may be independently determined based on the capture threshold of the atrial chamber, or else may be estimated based upon the ventricular defibrillation energy threshold or pacing energy threshold. For example, the atrial defibrillation energy threshold may be estimated as a predetermined percentage, such as one-tenth, one-fourth or one-half, of the ventricular defibrillation energy threshold.

Additionally, a defibrillation energy threshold tracking feature may be combined with an automatic defibrillation energy threshold estimation technique that is based on historical defibrillation information, such as described, for example, in U.S. patent application Ser. No. 09/981,652 filed Oct. 17, 2001, hereby incorporated by reference as if set forth fully herein. As an example, the defibrillation energy threshold may be estimated as an average or weighted average of the estimated defibrillation energy threshold based upon the pacing capture threshold, and the estimated defibrillation energy threshold based upon historical defibrillation information such as described in application Ser. No. 09/981,652 referenced above.

Although many embodiments have been described in connection with adjustment to defibrillation energy adjustments, it should be understood that similar adjustments to energy settings may be made, if necessary, for cardioverting shocks.

The various defibrillation threshold tracking methodologies employed herein are particularly advantageous for an implantable cardiac stimulation device, of the type which commonly operates autonomously for extended periods of time, but may also find use in external devices such as programmers or external pacing/defibrillation equipment. As a first example, a cardiac device programmer may use the foregoing methods at time of implant to measure or determine a pacing capture threshold, estimate the patient's defibrillation energy threshold based upon, e.g., the types of estimating equations described herein, and then use the estimated defibrillation energy threshold to program an implanted cardiac stimulation device. As a second example, a cardiac device programmer may use the foregoing methods at time of implant to measure or determine a pacing capture threshold, estimate the patient's defibrillation energy threshold based upon, e.g., the types of estimating equations described herein, and then provide the defibrillation threshold estimate to a physician through a conventional programmer interface to assist the physician in performing accurate and efficient defibrillation threshold testing as part of a patient's implant procedure.

While preferred embodiments of the invention have been described herein, many variations are possible which remain within the concept and scope of the invention. Such variations would become clear to one of ordinary skill in the art after inspection of the specification and the drawings. The invention therefore is not to be restricted except within the spirit and scope of any appended claims.

What is claimed is:

1. An implantable cardiac stimulating device comprising:
   a pulse generator that is operative to generate stimulating pulses to be applied to a patient's heart;
   a detection circuit that is operative to detect evoked responses from the patent's heart in response to applied stimulating pulses and to generate corresponding signals;
   a controller connected to the detection circuit and configured to determine a pacing stimulation threshold based on the signals from the detection circuit, and to derive an estimated defibrillation threshold value based upon the determined pacing stimulation threshold; and
   a memory operative to store the estimated defibrillation threshold value for use in a subsequent defibrillaton shock therapy.

2. The implantable cardiac stimulating device of claim 1, further comprising a defibrillation shock subsystem, the defibrillation shock subsystem utilizing the estimated defibrillation threshold value for a defibrillation shock therapy.

3. The implantable cardiac stimulating device of claim 1, wherein the controller is further configured to derive one or more defibrillation shock parameters using the estimated defibrillation threshold value.

4. The implantable cardiac stimulating device of claim 3, further comprising a memory for durably storing the one or more defibrillation shock parameters for use in a subsequent defibrillation shock therapy.

5. The implantable cardiac stimulating devic of claim 1, wherein the controller is configured to derive the estimated defibrillation threshold value using an estimating equation derived from a predictive regression formula.

6. The implantable cardiac stimulating device of claim 5, wherein the controller is configured to derive the estimated defibrillation threshold value substantially according to a formula of the form:

$$DFT = K1 + (K2 \times CPT)$$

wherein DFT represents the estimated defibrillation threshold value, and CPT represents the determined pacing stimulation threshold, and K1 and K2 both represent selected constants.

7. The implantable cardiac stimulating device of claim 6, wherein K1 has a value in a range of about 9 to 11, and wherein K2 has a value in a range of about 1,000 to 3,000, and wherein units of DFT and CFT are in terms of energy.

8. The implantable cardiac stimulating device of claim 1, wherein the controller is configured to derive the estimated defibrillation threshold value using an estimating equation derived from a multivariate regression formula.

9. The implantable cardiac stimulating device of claim 8, wherein the controller is configured to derive the estimated defibrillation threshold value substantially according to a formula of the form:

$$DFT=K1+(K2 \times CPT)-(K3 \times V1)-(K4 \times V2) \ldots (KN \times V(N-2))$$

wherein DFT represents the estimated defibrillation threshold value, CPT represents the determined pacing stimulation threshold, K1, K2, . . . KN represent selectable constants, and V1, V2, . . . V(N−2) represent variable parameters.

10. The implantable cardiac stimulating device of claim 9, wherein K1 has a value in a range of about 9 to 11 and K2 has a value in a range of about 1,000 to 3,000, and wherein units of DFT and CPT are in terms of energy.

11. The implantable cardiac stimulating device of claim 10, wherein variable parameter V1 represents the patient's age, variable parameter V2 represents the patient's gender, K3 has a value of about 1, and K4 has a value of about 1.

12. The implantable cardiac stimulating device of claim 1, wherein the controller is configured to repeat the operations of determining the pacing stimulation threshold and deriving the estimated defibrillation threshold value based thereon, so as to provide ongoing dynamic tracking of a patients defibrillation threshold after implantation.

13. The implantable cardiac stimulating device of claim 1, further comprising a memory durably storing a programmable scheduling parameter, the scheduling parameter corresponding to a time interval between periodic determinations of the pacing stimulation threshold.

14. The implantable cardiac stimulating device of claim 13, wherein the controller is configured to perform the operation of deriving the estimated defibrillation threshold value either periodically according to the scheduling parameter, or else on demand when the pacing stimulation threshold changes materially from its prior value.

15. The implantable cardiac stimulating device of claim 14, wherein the pacing stimulation threshold is deemed to have changed materially when it differs by more than a selected amount from its prior value.

16. The implantable cardiac stimulating device of claim 1, wherein the controller is configured to derive the estimated defibrillation threshold value based upon one or more variables in addition to the determined pacing stimulation threshold.

17. The implantable cardiac stimulating device of claim 16, wherein the one or more variables comprise the patient's gender.

18. The implantable cardiac stimulating device of claim 16, wherein the one or more variables comprise the patient's age.

19. The implantable cardiac stimulating device of claim 18, wherein the patient's age is adjusted for a duration in which the implanted cardiac stimulation device has been implanted.

20. The implantable cardiac stimulating device of claim 1, wherein the controller is configured to derive the estimated defibrillation threshold value by:

determining an initial estimated defibrillation threshold value based upon the determined pacing stimulation threshold; and adding a safety margin to the initial defibrillation threshold value.

21. The implantable cardiac stimulating device of claim 1, further comprising a lead incorporating a radioisotope material, the lead adapted for contact with the patient's heart.

22. A method for determining a patient's defibrillation energy threshold for an implanted cardiac stimulating device, the method comprising:

(a) determining a pacing stimulation threshold;

(b) deriving an estimated defibrillation threshold value based upon the determined pacing stimulation threshold; and (c) storing the estimated defibrillation threshold value for use in a subsequent defibrillation shock therapy.

23. The method of claim 22, further comprising utilizing the estimated defibrillation threshold value in a subsequent defibrillation shock therapy.

24. The method of claim 22, wherein (a), (b), and (c) are repeated so as to provide ongoing dynamic tracking of a patient's defibrillation threshold after implantation.

25. The method of claim 22, further comprising deriving one or more defibrillation shock parameters using the estimated defibrillation threshold value.

26. The method of claim 25, further comprising storing the one or more defibrillation shock parameters for use in a subsequent defibrillation shock therapy.

27. The method of claim 22, wherein deriving the estimated defibrillaton threshold value is carried out using an estimating equation derived from a predictive regression formula.

28. The method of claim 27, wherein deriving the estimated defibrillation threshold value is carried out substantially according to a formula of the form:

$$DFT=K1+(K2 \times CPT)$$

wherein DFT represents the estimated defibrillation threshold value, and CPT represents the determined pacing stimulation threshold, and K1 and K2 both represent selected constants.

29. The method of claim 28, wherein K1 has a value in a range of about 9 to 11, and wherein K2 has a value in a range of about 1,000 to 3,000, and wherein units of DFT and CPT are in terms of energy.

30. The method of claim 22, wherein deriving the estimated defibrillation threshold value is carried out using a multivariate regression formula.

31. The method of claim 30, wherein deriving the estimated defibrillation threshold value is carried out substantially according to a formula of the form:

$$DFT=K1+(K2 \times CPT)-(K3 \times V1)-(K4 \times V2) \ldots (KN \times V(N-2))$$

wherein DFT represents the estimated defibrillation threshold value, CPT represents the determined pacing stimulation threshold, K1, K2, . . . KN represent selectable constants, and V1, V2, . . . V(N−2) represent variable parameters.

32. The method of claim 31, wherein K1 has a value in a range of about 9 to 11, K2 has a value in a range of about 1,000 to 3,000, and units of DFT and CPT are in terms of energy.

33. The method of claim 32, wherein variable parameter V1 represents the patient's age, variable parameter V2 represents the patient's gender, K3 has a value of about 1, and K4 has a value of about 1.

34. The method of claim 22, wherein (a) is carried out periodically, and wherein a time interval between periodic determinations of the pacing stimulation threshold is selectable via a programmable scheduling parameter.

35. The method of claim 34, wherein (b) is carried out either periodically or else on demand when the pacing stimulation threshold determined in (a) has changed materially from its prior value.

36. The method of claim 35, wherein the pacing stimulation threshold is deemed to have changed materially when the pacing stimulation threshold determined in (a) differs by more than a selected amount from its prior value.

37. The method of claim 22, wherein deriving the estimated defibrillation threshold value is based upon one or more variables in addition to the determined pacing stimulation threshold.

38. The method of claim 37, wherein the one or more variables comprise the patent's gender.

39. The method of claim 37, wherein the one or more variables comprise the patient's age.

40. The method of claim 39, wherein the patient's age is adjusted for a duration in which the implanted cardiac stimulation device has been implanted.

41. The method of claim 22, wherein deriving the estimated defibrillation threshold value comprises:
   determining an initial estimated defibrillation threshold value based upon the pacing energy stimulation threshold determined in (a); and
   adding a safety margin to the initial defibrillation threshold value.

42. The method of claim 22, wherein the implanted cardiac stimulation device comprises a lead incorporating a radioisotope material.

43. An implantable cardioverter/defibrillator (ICD), comprising:
   at least one terminal that is configured to be connected to a lead adapted for placement in proximity of a patient's heart;
   a pulse generator that is operative to generate stimulating pulses for delivery to the patient's heart via the at least one terminal;
   a detection circuit connected to the at least one terminal that is operative to detect an evoked response of the heart in response to a stimulating pulse;
   a high voltage defibrillation shock subsystem adapted for delivery of high voltage shocks to the patient's heart;
   a controller, the controller configured to derive an estimated defibrillation energy threshold value based upon a determined pacing stimulation threshold; and
   a memory that stores the estimated defibrillation energy threshold value.

44. The implantable cardioverter/defibrillator of claim 43, wherein the controller is configured to derive the estimated defibrillation energy threshold value from either a predictive regression formula or a multivariate regression formula.

45. The implantable cardioverter/defibrillator of claim 43, wherein the controller is further configured to a pacing stimulation threshold value at periodic intervals, according to a programmed schedule.

46. The implantable cardioverter/defibrillator of claim 45, wherein the controller is further configured to derive the estimated defibrillation energy threshold value according to the programmed schedule.

47. The implantable cardioverter/defibrillator of claim 45, wherein the controller is further configured to derive the estimated defibrillation energy threshold value on demand when the pacing stimulation threshold differs materially from its prior value.

48. An implantable cardiac stimulation device, comprising:
   means for generating stimulating pulses for application to a patient's heart;
   means for determining a pacing stimulation threshold;
   means for deriving a defibrillation threshold value as a function of the determined pacing stimulation threshold; and
   means for storing the derived defibrillation threshold value for use in a subsequent defibrillation shock therapy.

49. A method for automatically determining a patient's defibrillation threshold for a cardiac stimulating device, the method comprising:
   (a) determining a pacing stimulation threshold through application of pacing pulses to a patent's heart;
   (b) deriving an estimated defibrillation energy threshold value based upon the pacing stimulation threshold; and
   (c) storing the estimated defibrillation threshold value for use in a subsequent defibrillation shock therapy.

50. The method of claim 49, further comprising calculating one or more defibrillation shock parameters from the estimated defibrillation energy threshold value.

51. The method of claim 49, wherein (a) and (b) are performed by an external cardiac device programmer, the method further comprising:
   transmitting the estimated defibrillation threshold, or defibrillation shock parameters derived therefrom, from the external cardiac device programmer to an implantable cardiac stimulation device.

* * * * *